(12) United States Patent
Sharabani et al.

(10) Patent No.: US 10,842,641 B2
(45) Date of Patent: Nov. 24, 2020

(54) EXPANDABLE IMPLANT WITH DEFLECTABLE SEQUENCE OF SEGMENTS

(71) Applicant: SEASPINE, INC., Carlsbad, CA (US)

(72) Inventors: Netanel Sharabani, Rishpon (IL); Nadav Lavochkin, Hadera (IL); Oded Loebl, Tel-Mond (IL)

(73) Assignee: SeaSpine, Inc., Carlsbad, CA (US)

( * ) Notice: Subject to any disclaimer, the term of this patent is extended or adjusted under 35 U.S.C. 154(b) by 94 days.

(21) Appl. No.: 15/741,294

(22) PCT Filed: Jul. 14, 2016

(86) PCT No.: PCT/IL2016/050762
§ 371 (c)(1),
(2) Date: Jan. 2, 2018

(87) PCT Pub. No.: WO2017/009840
PCT Pub. Date: Jan. 19, 2017

(65) Prior Publication Data
US 2018/0185164 A1 Jul. 5, 2018

Related U.S. Application Data

(60) Provisional application No. 62/192,084, filed on Jul. 14, 2015.

(51) Int. Cl.
*A61F 2/44* (2006.01)
*A61F 2/30* (2006.01)

(52) U.S. Cl.
CPC ............ *A61F 2/4425* (2013.01); *A61F 2/442* (2013.01); *A61F 2/447* (2013.01); *A61F 2/4455* (2013.01);

(Continued)

(58) Field of Classification Search
CPC .................................. A61F 2/44; A61F 2/4425
See application file for complete search history.

(56) References Cited

U.S. PATENT DOCUMENTS

| 8,663,329 B2 * | 3/2014 | Ernst ..................... A61F 2/4465 |
| | | 623/17.15 |
| 2010/0249935 A1 * | 9/2010 | Slivka ................... A61F 2/4684 |
| | | 623/17.16 |

(Continued)

FOREIGN PATENT DOCUMENTS

| WO | 2015063719 A1 | 5/2015 |
| WO | 2017009840 A1 | 1/2017 |

OTHER PUBLICATIONS

Israel Patent Office, International Search Report and Written Opinion for PCT/IL2016/050762 dated Oct. 5, 2016, 8 pages.

*Primary Examiner* — Christopher J Beccia
(74) *Attorney, Agent, or Firm* — Middleton Reutlinger

(57) ABSTRACT

An implant (100, 200, 300, 400) includes a base (10), and a sequence of at least two segments including a first segment (12) and a last segment (14). The first segment (12) is pivotally linked to base (10). Adjacent segments are interconnected at pivotal connections (18). A bolt (20) has a threaded shaft (22) and a head (24). The threaded shaft (22) is engaged in a threaded channel (26) of the base (10) so that rotation of the bolt (20) about a central axis of the threaded shaft (22) varies a degree of overlap between the base (10) and the bolt (20). The last segment (14) and the head (24) define therebetween a spherical bearing (28). Rotation of bolt (20) thus varies a distance between spherical bearing (28) and hinge pin (16), thereby causing deflection of the sequence of segments.

7 Claims, 11 Drawing Sheets

(52) U.S. Cl.
CPC ............... *A61F 2002/3055* (2013.01); *A61F 2002/30405* (2013.01); *A61F 2002/30433* (2013.01); *A61F 2002/30471* (2013.01); *A61F 2002/30507* (2013.01); *A61F 2002/30538* (2013.01); *A61F 2002/30556* (2013.01); *A61F 2002/30904* (2013.01); *A61F 2002/443* (2013.01)

(56) References Cited

U.S. PATENT DOCUMENTS

| | | |
|---|---|---|
| 2011/0077738 A1 | 3/2011 | Ciupik et al. |
| 2016/0120660 A1* | 5/2016 | Melkent ............... A61F 2/4455 623/17.16 |

* cited by examiner

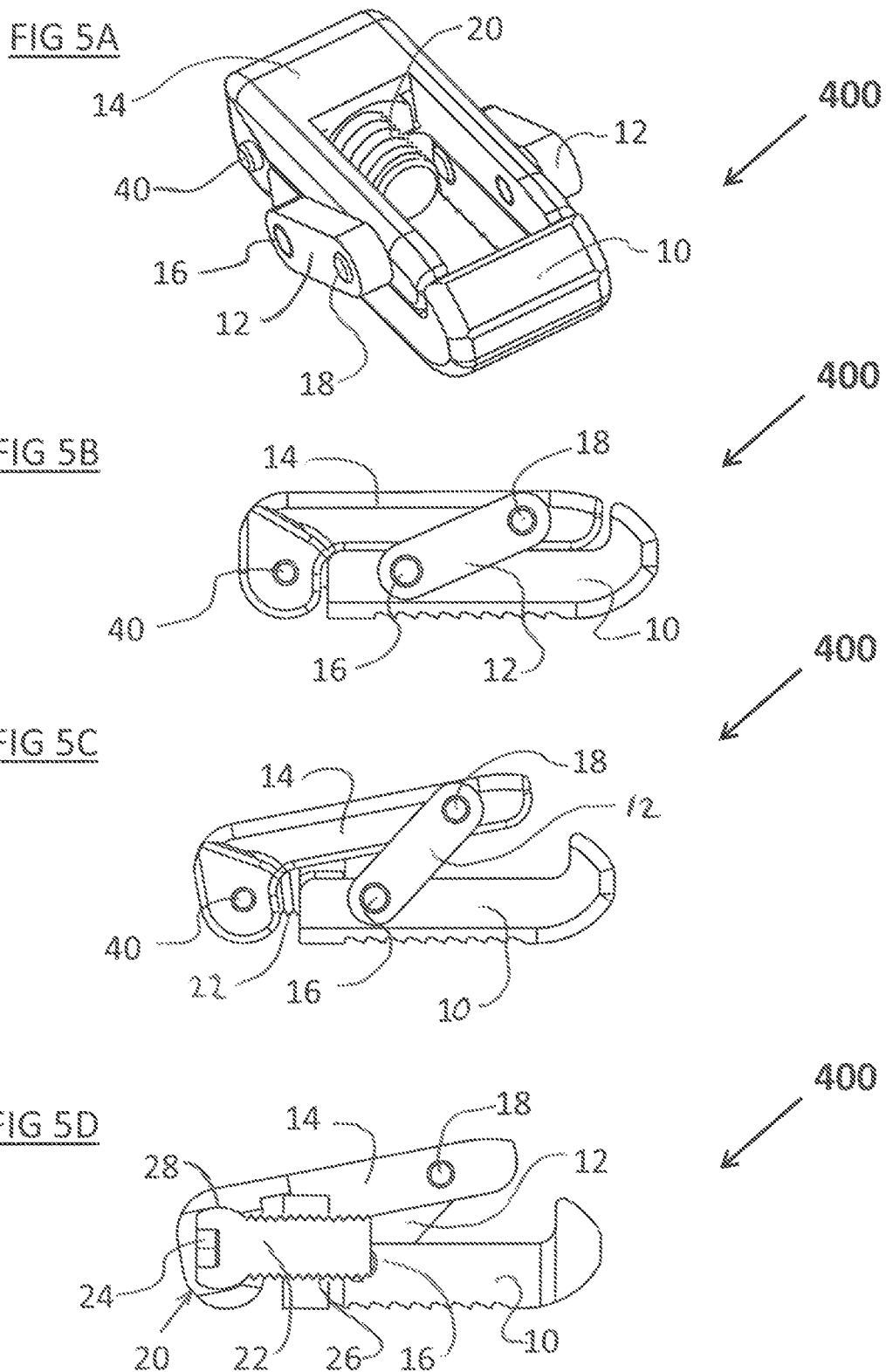

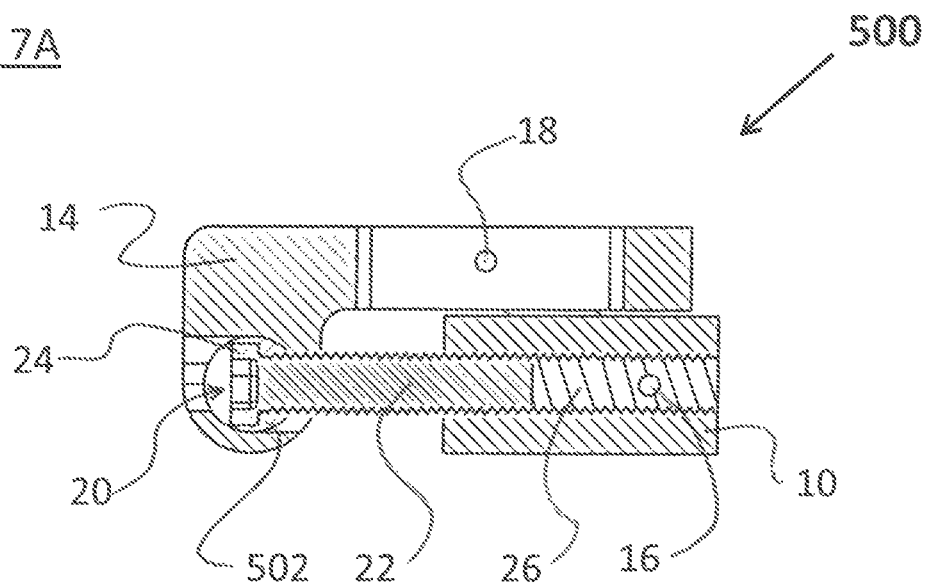
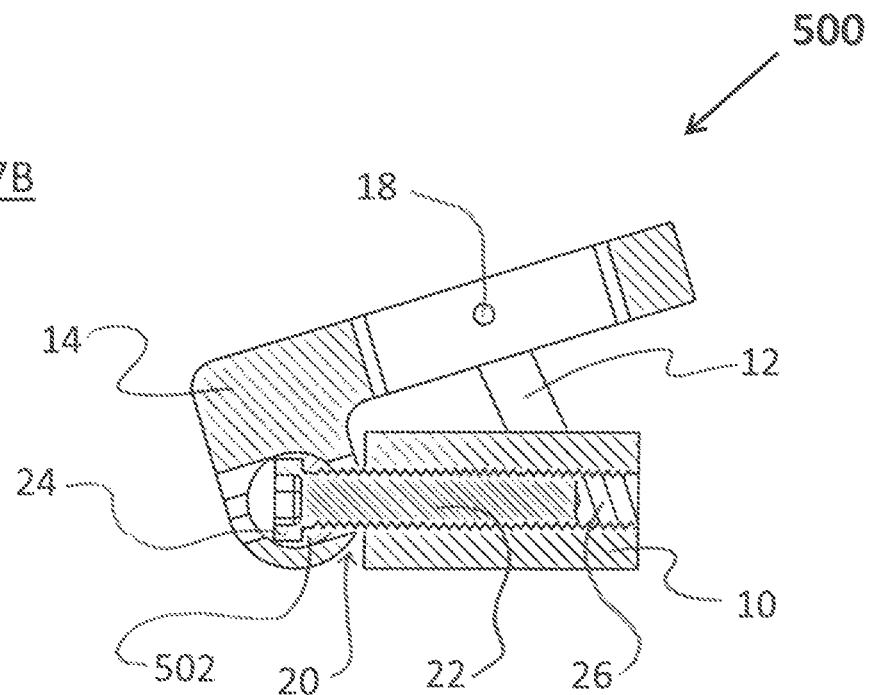

FIG. 8 – Table of Vertical parallel movement applications:
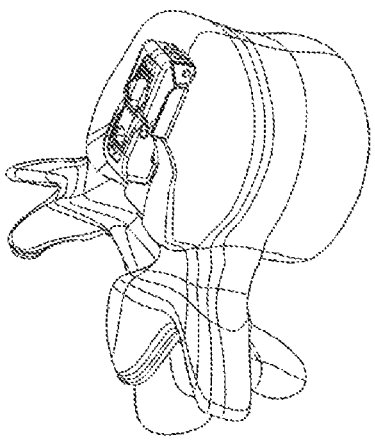

FIG. 9 - Table of Horizontal parallel movement applications:

| | ALIF AND PLIF APPROACHES FOR HORIZONTAL EXPANSION | LLIF APPROACH FOR HORIZONTAL EXPANSION | TLIF AND OLIF APPROACHES FOR HORIZONTAL EXPANSION |
|---|---|---|---|
| FLAT CONFIGURATION | | | |
| EXPANDED CONFIG. | CAN OPEN ANTERIORLY OR POSTERIORLY (SHOWN) | CAN OPEN ANTERIORLY OR POSTERIORLY (SHOWN) | CAN OPEN ANTERIORLY OR POSTERIORLY (SHOWN) |

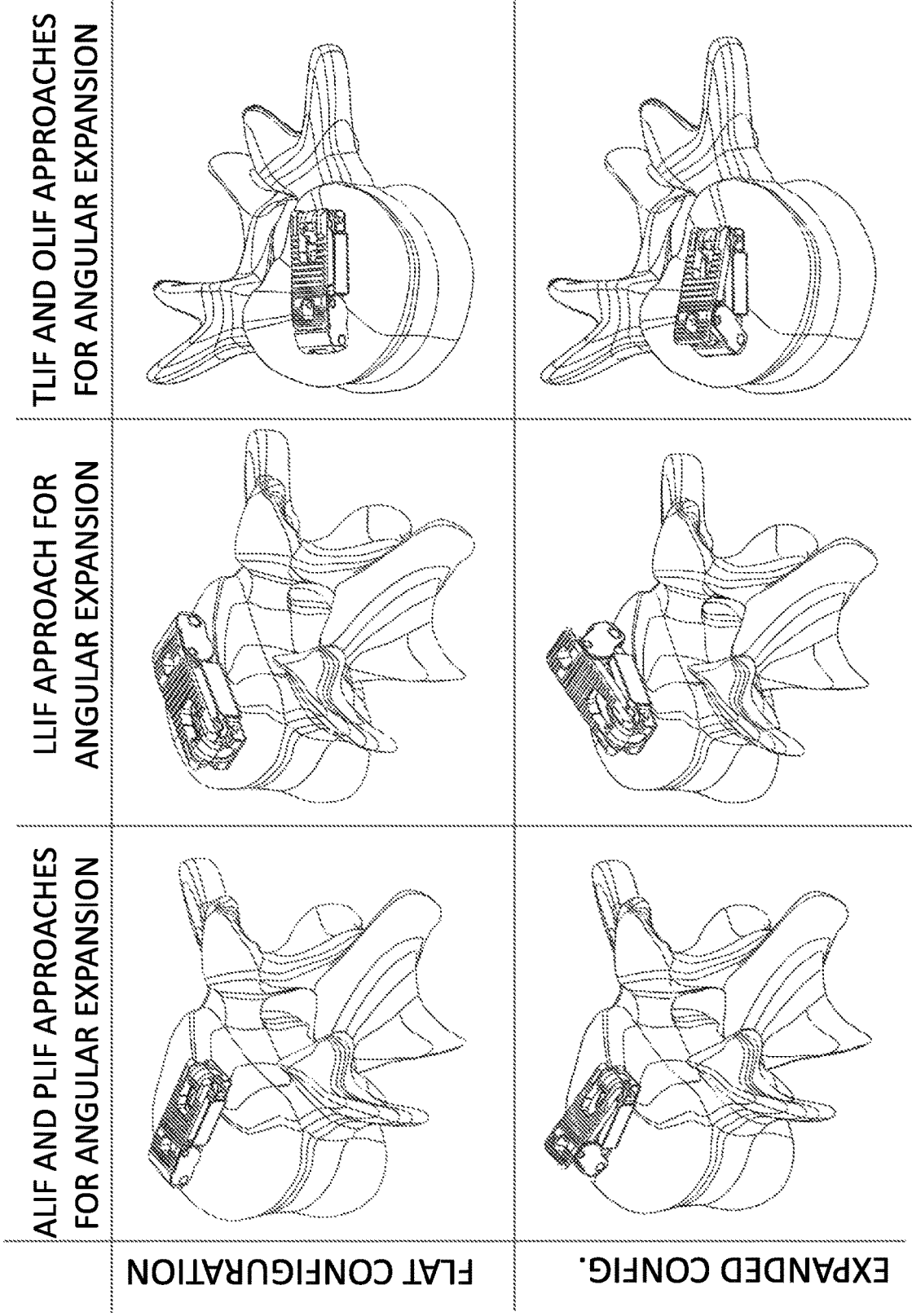
FIG. 10 - Table of Vertical Angular movement applications:

FIG. 11 – Table of Horizontal Angular motion applications:
| ALIF AND PLIF APPROACHES FOR HORIZONTAL EXPANSION | LLIF APPROACH FOR HORIZONTAL EXPANSION | TLIF AND OLIF APPROACHES FOR HORIZONTAL EXPANSION |
|---|---|---|
| 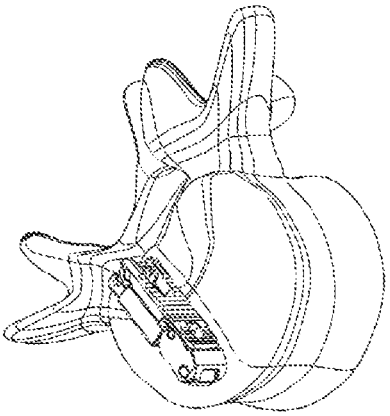 | 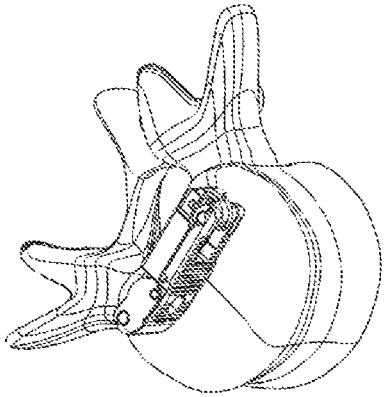 | 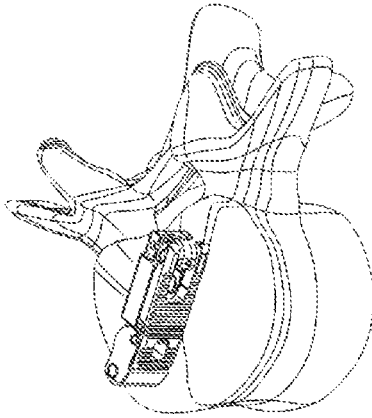 FLAT CONFIGURATION |
| 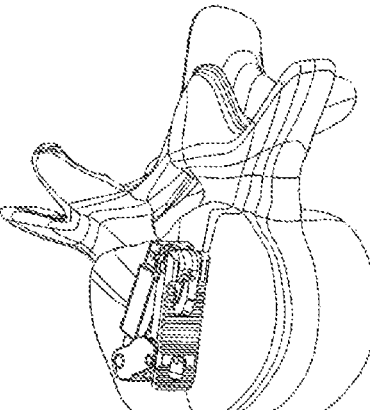 | 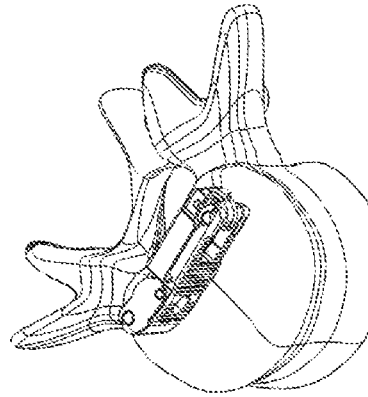 | 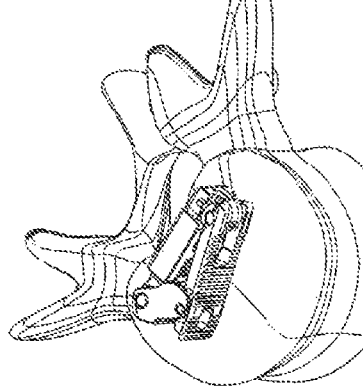 EXPANDED CONFIG. CAN OPEN IN THE POSTERIOR OR ANTERIOR DIRECTION (SHOWN) |

EXPANDABLE IMPLANT WITH DEFLECTABLE SEQUENCE OF SEGMENTS

FIELD AND BACKGROUND OF THE INVENTION

The present invention relates to implants and, in particular, it concerns an expandable implant with a deflectable sequence of segments.

Various expanding implants are described in prior patents and patent publications commonly assigned with the present invention, which provide the most relevant background to the present invention. The publications mentioned herein are not to be considered prior art other than to the extent that they are defined as such by the applicable patent laws for the national phase of any application stemming from this international application. Such documents include: U.S. Pat. No. 9,005,291 B2; U.S. Pat. No. 9,017,413 B2; International Publication No. WO 2015/063719 A1; and International Publication No. WO 2016/063283 A1.

In general terms, these examples disclose various forms of an adjustable implant which includes a telescopic body with first and second portions in sliding engagement, and a deflectable linkage connected between the two portions of the base. The deflectable linkage is formed from at least two segments in pivotal interconnection so that adjustment of a length of the telescopic body causes a corresponding deflection of the deflectable linkage. Such implants find a range of applications, particularly where it is desired to insert an implant in a relatively low-profile state and subsequently expand the implant. Where a linkage with three segments is used, an intermediate segment is typically enlarged and provides a contact surface facing outwards such that adjustment of the implant can achieve tissue distraction. Where two segments are used, one of which is enlarged, the device can be used for adjusting an angular relationship between two facing regions of tissue. Such implants find particularly valuable applications in the field of spinal surgery, for example, for insertion into an intervertebral space to achieve axial distraction, lordotic correction and/or correction of scoliosis.

SUMMARY OF THE INVENTION

The present invention is an expandable implant with a deflectable sequence of segments.

According to the teachings of an embodiment of the present invention there is provided, an implant comprising: (a) a base; (b) a sequence of at least two segments including a first segment and a last segment, the first segment being pivotally linked to the base, adjacent segments of the sequence of segments being interconnected at pivotal connections; and (c) a bolt having a threaded shaft with a central axis and a head, the threaded shaft being engaged in a threaded channel of the base, wherein the last segment and the head define therebetween a spherical bearing such that rotation of the bolt about the central axis varies a degree of overlap between the base and the bolt, and causes deflection of the sequence of segments.

According to a further feature of an embodiment of the present invention, the sequence comprises only two segments.

According to a further feature of an embodiment of the present invention, a first of the two segments extends along a majority of a length of the sequence, and a second of the two segments extends along less than half of the length of the sequence.

According to a further feature of an embodiment of the present invention, the first segment and the second segment are interconnected at a pivot axis, and the pivot axis is located within a medial 50% of a length of the first segment.

According to a further feature of an embodiment of the present invention, the sequence includes three segments.

According to a further feature of an embodiment of the present invention, the three segments comprise a major intermediate segment and first and last linking segments.

According to a further feature of an embodiment of the present invention, there is also provided a gear-tooth engagement to preserve parallel orientation of the intermediate segment to the base.

There is also provided according to an embodiment of the present invention, an implant comprising: (a) a base; (b) a sequence of at least two segments including a first segment and a last segment, the first segment being pivotally linked to the base, and the sequence of segments being sequentially pivotally linked; (c) a core rotatably mounted within a transverse bore through the last segment, the core having a socket; and (d) a bolt having a threaded shaft and a head, the bolt being engaged in the socket of the core with the threaded shaft projecting therefrom, the threaded shaft being engaged in a threaded channel of the base, such that rotation of the bolt changes a degree of overlap between the base and the bolt, and causes deflection of the sequence of segments.

According to a further feature of an embodiment of the present invention, the sequence includes only two segments comprising one major segment and one linking segment.

According to a further feature of an embodiment of the present invention, the sequence includes three segments.

According to a further feature of an embodiment of the present invention, the three segments comprise a major intermediate segment and first and last linking segments.

According to a further feature of an embodiment of the present invention, there is also provided a gear-tooth engagement to preserve parallel orientation of the intermediate segment to the base.

BRIEF DESCRIPTION OF THE DRAWINGS

The invention is herein described, by way of example only, with reference to the accompanying drawings, wherein:

FIG. 5A is an isometric view of a further implant, constructed and operative according to an aspect of the present invention, shown in a low profile state;

FIGS. 5B and 5C are side views of the implant of FIG. 5A, shown in a low profile state and a partially expanded state, respectively;

FIG. 5D is a longitudinal cross-sectional view taken through the implant of FIG. 5C in its partially expanded state;

FIGS. 7A and 7B are longitudinal cross-sectional views taken through the implant of FIGS. 6B and 6C, shown in a low profile state and a fully expanded state, respectively;

FIG. 8 is a table containing schematic illustrations of applications employing the implant of FIGS. 1A-2C in a range of intervertebral applications with expansion in a vertical (axial) direction, the implant being shown in a low-profile insertion configuration and an expanded configuration, respectively;

FIG. 9 is a table containing schematic illustrations of applications employing the implant of FIGS. 1A-2C in a range of intervertebral applications with expansion in a transverse (lateral) direction, the implant being shown in a low-profile insertion configuration and an expanded configuration, respectively;

FIG. 10 is a table containing schematic illustrations of applications employing the implant of FIGS. 3A-3C in a range of intervertebral applications with angular expansion in a vertical (axial) direction, the implant being shown in a low-profile insertion configuration and an expanded configuration, respectively; and FIG. 11 is a table containing schematic illustrations of applications employing the implant of FIGS. 3A-3C in a range of intervertebral applications with angular expansion in a transverse (lateral) direction, the implant being shown in a low-profile insertion configuration and an expanded configuration, respectively.

DESCRIPTION OF THE PREFERRED EMBODIMENTS

The present invention is an expandable implant with a deflectable sequence of segments.

The principles and operation of implants according to the present invention may be better understood with reference to the drawings and the accompanying description.

Figure 1A:
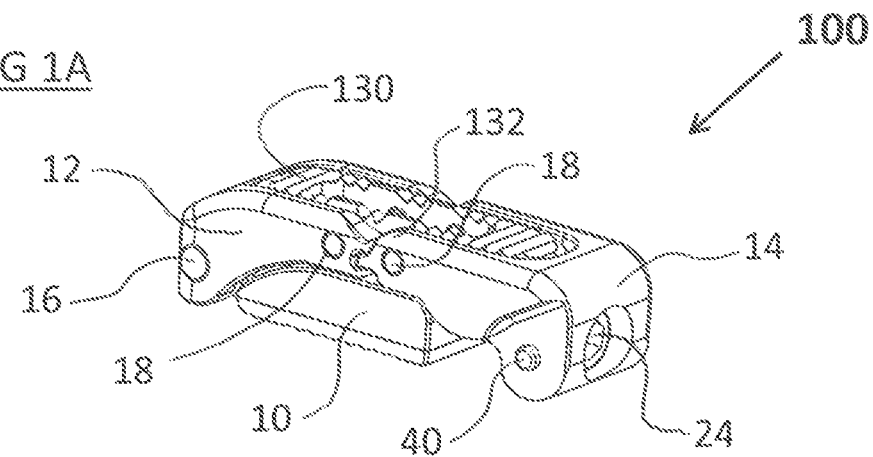
FIGS. 1A-1C are isometric views of an implant, constructed and operative according to an aspect of the present invention, shown in a low profile state, a partially expanded state and a fully expanded state, respectively.
Figure 1B:
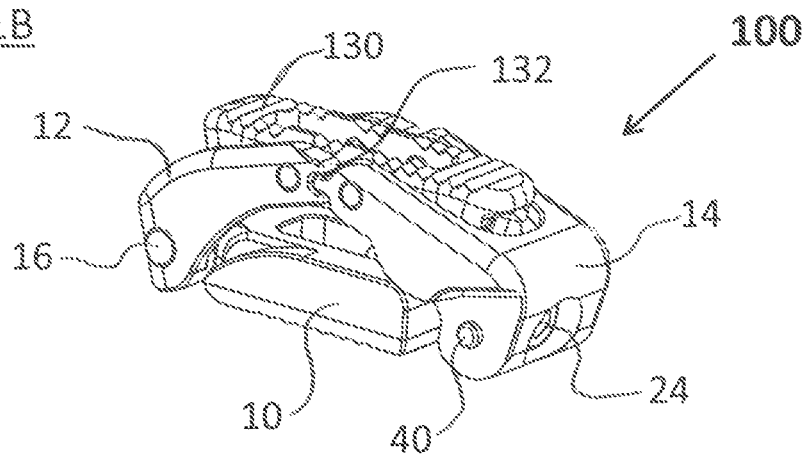
Figure 1C:
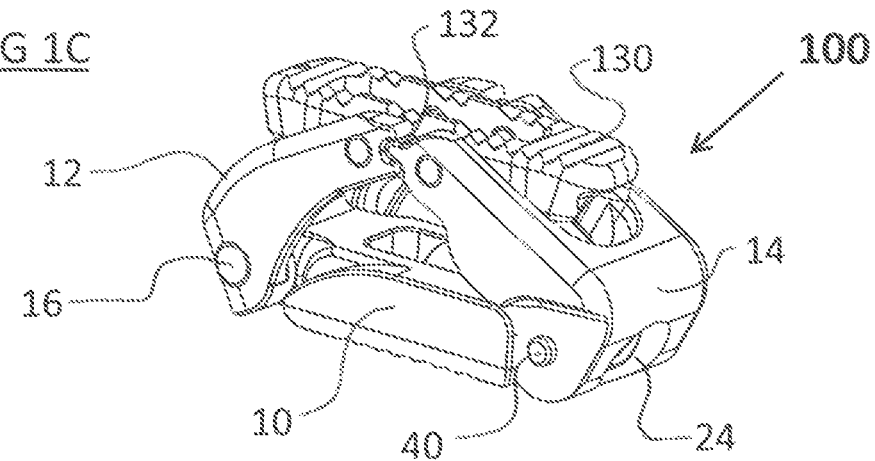
Figure 2A:
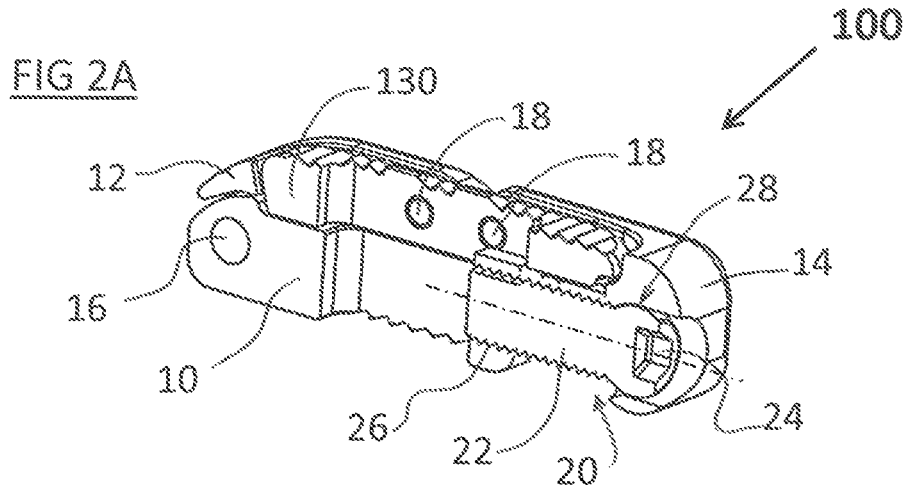
FIGS. 2A-2C are longitudinal cross-sectional views taken through the implant as shown in FIGS. 1A-1C, respectively.
Figure 2B:
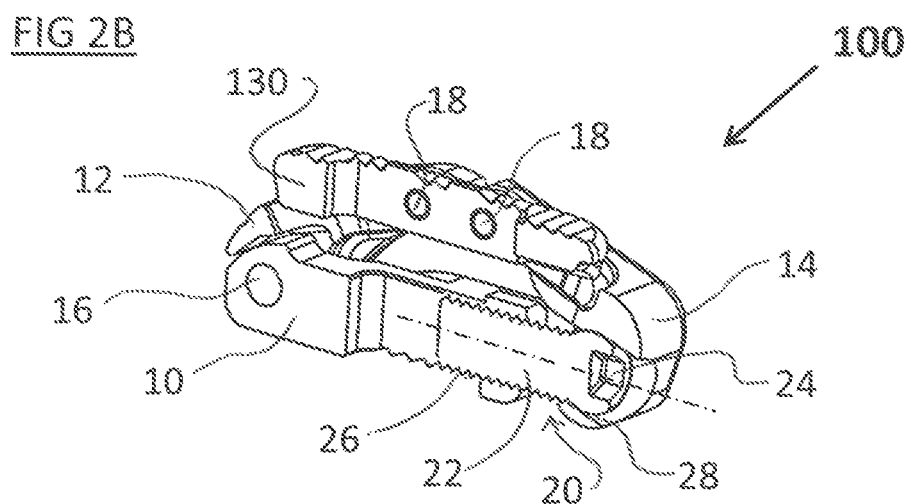
Figure 2C:
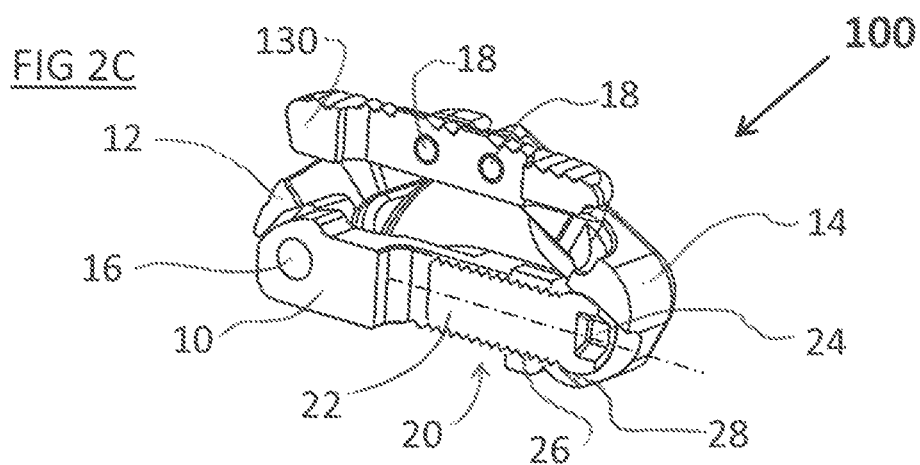
Figure 3A:
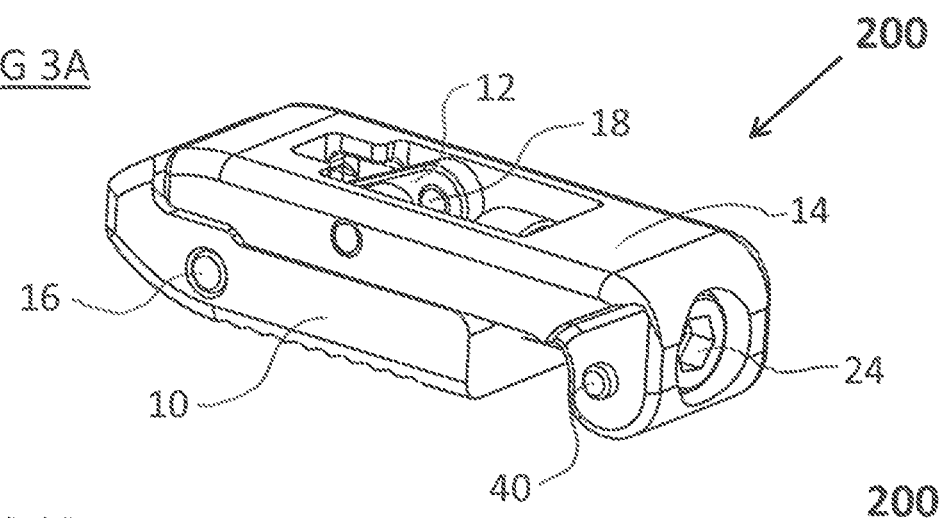
FIG. 3A is an isometric view of a further implant, constructed and operative according to an aspect of the present invention, shown in a low profile state.
Figure 3B:
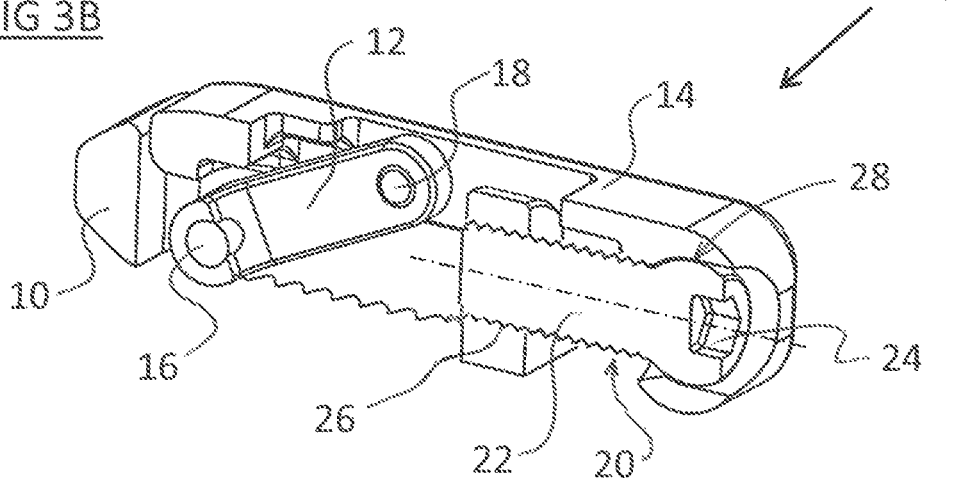
FIGS. 3B and 3C are longitudinal cross-sectional views taken through the implant of FIG. 3A, shown in a low profile state and a partially expanded state, respectively.
Figure 3C:
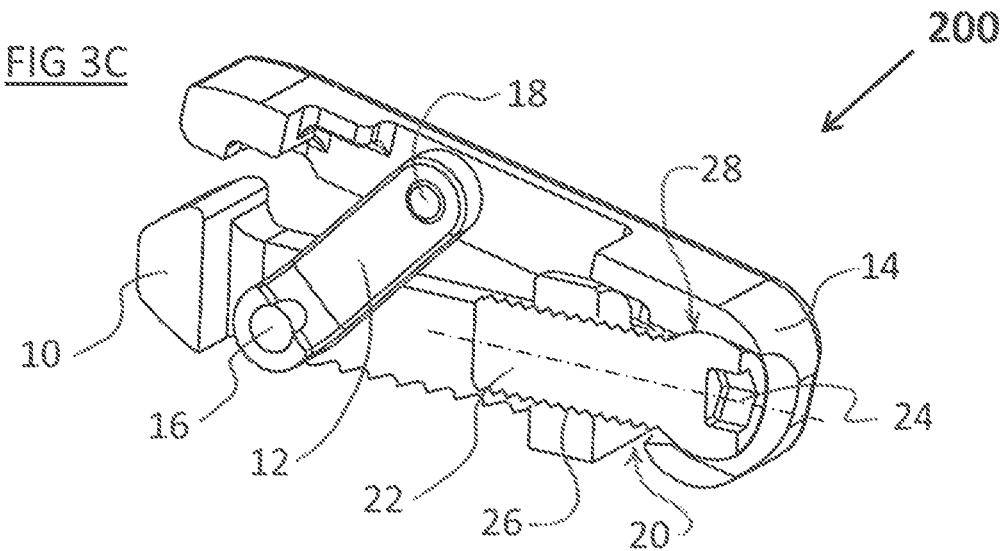
Figure 4A:
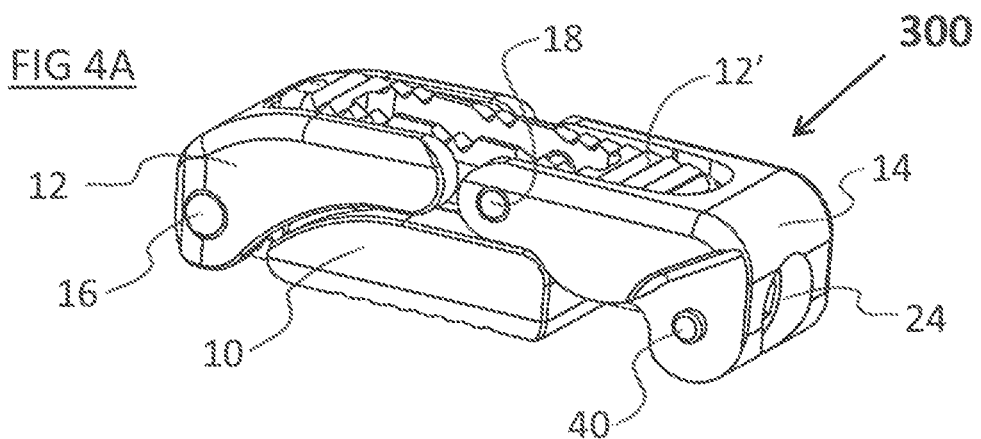
FIG. 4A is an isometric view of a further implant, constructed and operative according to an aspect of the present invention, shown in a low profile state.
Figure 4B:
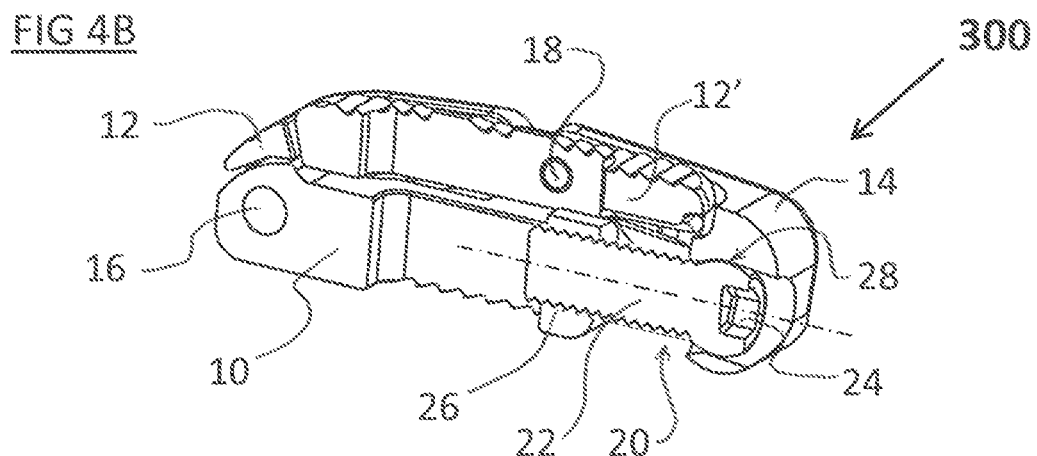
FIGS. 4B and 4C are longitudinal cross-sectional views taken through the implant of FIG. 4A, shown in a low profile state and a partially expanded state, respectively.
Figure 4C:
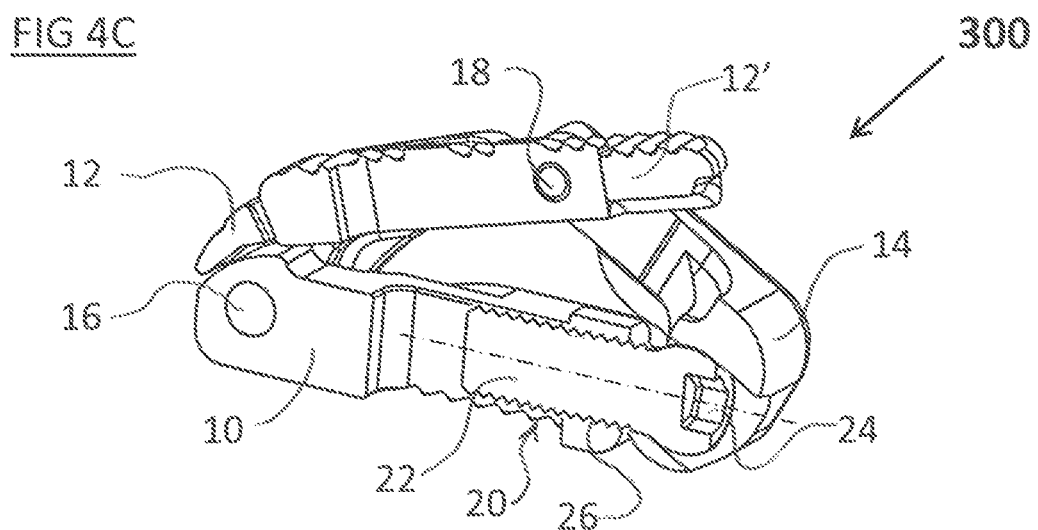

Referring now to the drawings, a first aspect of the present invention is referred to firstly in terms generic to the various embodiments of an implant 100, 200, 300 and 400 illustrated in FIGS. 1A-5D. Specifically, these figures each show an implant 100, 200, 300 or 400 having a base 10, and a sequence of at least two segments including a first segment 12 and a last segment 14. First segment 12 is pivotally linked to base 10, for example, via a hinge pin 16 or other pivotal interconnection. Adjacent segments of the sequence of segments are interconnected at pivotal connections 18. A bolt 20 has a threaded shaft 22 and a head 24. Threaded shaft 22 is engaged in a threaded channel 26 of base 10 so that rotation of bolt 20 about a central axis of threaded shaft 22 varies a degree of overlap between base 10 and bolt 20. Last segment 14 and head 24 define therebetween a spherical bearing 28. Rotation of bolt 20 thus varies a distance between spherical bearing 28 and hinge pin 16, thereby causing deflection of the sequence of segments.

The term "spherical bearing" is used herein to refer to a bearing in which the contact surfaces presented by last segment 14 for abutment of head 24 of bolt 20 correspond to partial spherical surfaces, thereby facilitating both a rotating motion of bolt 20 about its central axis and a pivotal motion of last segment 14 about a center of the "sphere" in all rotational positions of the bolt. Most preferably, the complementary surfaces of head 24 are also partial spherical surfaces in order to distribute loading over an extended contact region, rather than just along a line of contact. Most preferably, the partial-spherical bearing surfaces of last segment 14 correspond to two strips of a cylindrical surface on either side of a slot sized to allow the shaft of the bolt to extend therebetween.

The use of a bolt with spherical bearings provides a particularly elegant implementation of an expandable implant, typically reducing the number of components of the implant compared to a similar implant with a telescopic base and a separate adjustment mechanism and/or locking mechanism.

The term "segment" as used herein refers to a rigid structure which bridges between two pivotal connections, and may extend beyond those connections. Each segment may be a single central structure, or may be a forked structure which extends on either side of another segment. In some cases, the function of a single "segment" is provided by a pair of parallel arms which are not directly interconnected. Any such structures which bridge between the same two pivot axes and move together are referred to herein as a single segment.

The various pivotal connections, including pivotal connection 16 between base 10 and first segment 12 and pivotal connections 18 between adjacent segments, may be implemented in any desired manner, whether by use of a separate hinge pin which engages apertures in both elements, or by formation of an integral pin or other engagement features in one of the elements which engages an aperture in the other. A single pin may traverse the center of the implant, or the engagement may be bilateral, with separate pins on each side of the implant.

Depending upon the intended application and deployment location, the implants of the present invention are typically formed with various openings, for example, to allow filling with material for promoting bone growth and/or for ingrowth of bone or other tissue such as for osteo-integration. The locations, orientations and size of the various openings or windows will be readily chosen by a person having ordinary skill in the art according to the details of the intended application.

Similarly, the implants typically include various features for facilitating manipulation of the implant by an implant holder device, as exemplified by projecting pins 40 illustrated in certain embodiments below.

Turning now to the specific exemplary embodiments of this aspect of the present invention, FIGS. 1A-2C illustrate an implant 100 in which the sequence of segments includes three segments, one of which is a major intermediate segment 130 which is pivotally linked to first and last segments 12 and 14, which are implemented as linking segments. In this context, a "major segment" refers to a segment which extends along a length of at least 50% of the total length of the implant in its collapsed state, and more typically, in excess of 70%, and most preferably in excess of 80%. The term "linking segment" is used to refer to segments which each extend no more than about 55% of the length of the implant in its collapsed state, and most preferably no more than about 50%. Additionally, the "major segment" typically extends in both directions at least about 10% of its length beyond the location of pivotal connections 18 whereas the "linking segments" typically extend less than 10% of their respective lengths beyond the locations of pivotal connections 18.

This three-segment embodiment is typically configured to generate roughly parallel expansion in the sense that a lower surface of the base and an upper surface of the major segment are initially roughly parallel (subject to modification for conforming to anatomical feature with which they are to fit and/or bone purchasing features or the like) and undergo a roughly linear (parallel) expansion so that the angle between the outward facing surfaces does not significantly change as they move apart. As a result, this embodiment and variations thereof are highly suited to various tissue extraction and expansion applications, including but not limited to, intervertebral height restoration as part of a fusion procedure, or vertebral body height restoration as part of a kyoplasty procedure. It can also be used to advantage for in-plane expansion as an implant with a low-profile insertion state which is subsequently expandable. A subset of possible applications for vertical and in-plane expansion are illustrated schematically in the tables of FIGS. 8 and 9, for a range of different approach modalities and applications.

In certain cases, implant 100 may advantageously include additional features for helping to maintain a parallel orientation of the intermediate segment relative to the base. In the case illustrated here, first and last segments 12 and 14 are formed with a gear-tooth engagement configuration 132 to preserve parallel orientation of the intermediate segment to the base. Further details of this solution may be found in the description of the aforementioned International Publication No. WO 2016/063283 A1.

Turning now to FIGS. 3A-3C and 4A-4C, these illustrate two further implants 200 and 300 that correspond to the generic description above, but in these cases implemented with a sequence of segments including only two segments, namely, first segment 12 and last segment 14, that are directly pivotally attached at pivotal connection 18. Preferably, a first of the two segments is a "major segment" extending along a majority of the length of the sequence, and a second of the two segments is a "linking segment", preferably extending along less than half of the length of the sequence. Pivot axis 18 between the two segments is most preferably located within a medial 50% of a length of the major segment, i.e., at a location between 25% and 75% of the length of the segment from one of the ends.

In the case of implant 200, last segment 14 is the major segment while first segment 12 is the linking segment. As a result, the functionality of implant 200 is to provide angular opening between the lower surface of the base and the upper surface of the major segment where the opening occurs primarily through a separation of the contact surfaces at the distal end of the device. This configuration would be particularly suitable, for example, for restoration of a lordotic angle between adjacent vertebral bodies where the implant is inserted from a posterior (e.g., PLIF or TLIF) approach to generate increased separation in an anterior region of the intervertebral space, or for correction of scoliosis where increased elevation is required at the side furthest from the insertion opening.

In the case of implant 300, first segment 12 is the major segment while last segment 14 is the linking segment. In this non-limiting example, first segment 12 is formed from a forked portion of structure similar to last segment 14 rigidly integrated (welded or integrally formed) with an extended contact surface portion 12'. As a result, the functionality of implant 300 is to provide angular opening between the lower surface of the base and the upper surface of the major segment where the opening occurs primarily through a separation of the contact surfaces at the proximal end of the device. This configuration would be particularly suitable, for example, for restoration of a lordotic angle between adjacent vertebral bodies where the implant is inserted from an anterior approach to generate increased separation in an anterior region of the intervertebral space, or for correction of scoliosis where increased elevation is required at the side closest to the insertion opening.

These embodiments can also be used for in-plane expansion. A subset of possible applications for vertical and in-plane angular expansion are illustrated schematically in the tables of FIGS. 10 and 11, for a range of different approach modalities and applications.

Turning now to FIGS. 5A-5D, it should be noted that implementations of the present invention may be configured to employ bolt 20 to expand the implant when increasing overlap with base 10, as illustrated above, or when decreasing overlap with base 10. By way of example, implant 400 is conceptually and functionally similar to implant 200 in that it employs a two-segment sequence in which last segment 14 is a major segment and first segment 12 is a linking segment. In this case, pivot 16 is located closer to head 24 of bolt 20 than pivot 18, and spherical bearing 28 is configured to oppose extensional forces of bolt head 24, i.e., that push last segment 14 along the axial direction of the bolt away from base 10. This together with an initial offset of pivot 18 above pivot 16 results in a pivotal opening motion of major segment 14 as bolt 20 is actuated by rotation about its central axis to recede from base 10.

It should be noted that this alternative form of actuation, as the bolt withdraws from base 10, may equally be implemented in any of the other configurations described herein, as will be clear to a person having ordinary skill in the art.

Figure 6A:
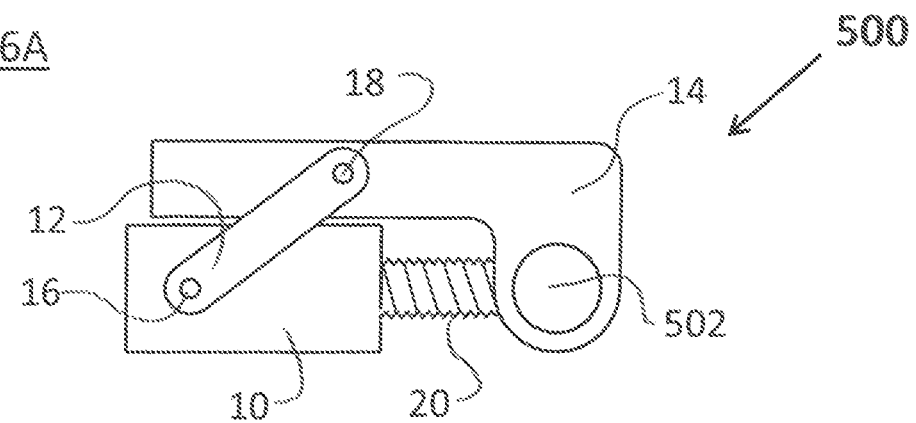
FIG. 6A is a side view of a further implant, constructed and operative according to an aspect of the present invention, shown in a low profile state.
Figure 6B:
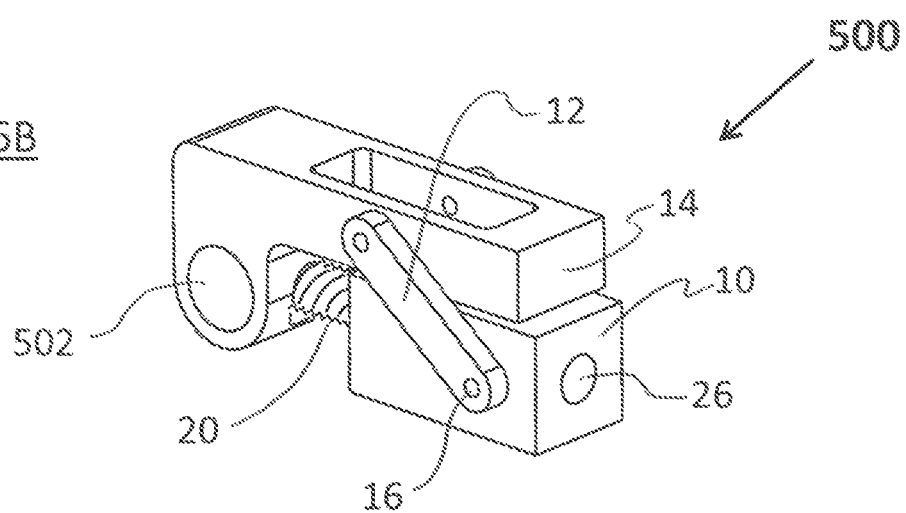
FIGS. 6B and 6C are isometric views of the implant of FIG. 6A, shown in a low profile state and a fully expanded state, respectively.
Figure 6C:
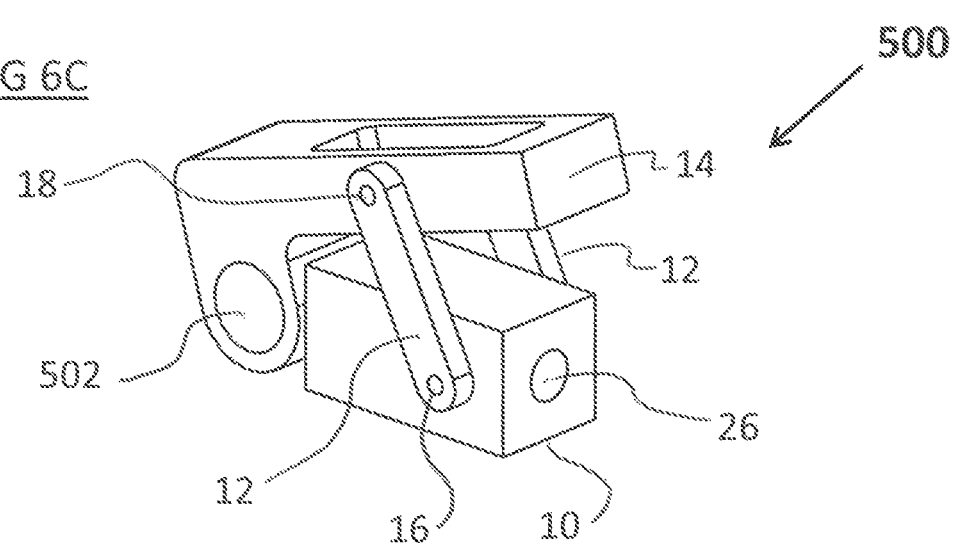

Turning now to FIGS. 6A-7B, in the embodiments of the invention presented thus far, the combined motions of rotation of bolt 20 and pivoting of last segment 14 relative to the head of the bolt are accommodated by use of a spherical bearing. These drawings illustrate an implant 500 with an alternative configuration for accommodating such motion.

Specifically, FIGS. 6A-7B illustrate schematically an implant 500 that is generally similar to implant 200 described above, with equivalent components labeled similarly. Thus implant 500 has a base 10, a sequence of at least two segments including a first segment 12 and a last segment 14, where first segment 12 is pivotally linked to base 10 at pivot axis 16, and the sequence of segments are pivotally linked at 18. In this case, the sequence employs only two independent segments, providing angular adjustment functionality similar to that of implant 200, although forms such as implants 100, 300 and 400 can also be implemented according to the principles of this embodiment.

Implant 500 differs from implant 200 primarily in the form of interconnection between bolt 20 and last segment 14. In this case, pivotal motion of last segment 14 relative to bolt 20 is accommodated by a core 502 that is rotatably mounted within a transverse bore through last segment 14. Core 502, which is typically cylindrical, has a socket 504 for receiving the head of bolt 20. Specifically, threaded shaft 22 of bolt 20 passes through an aperture formed in core 502 and head 24 is seated in socket 504 of core 502 so that threaded shaft 22 projects from the core and head 24 is rotatably within socket 504. Threaded shaft 22 is engaged in a threaded channel 26 of base 10. Bolt 20 is seated in core 502 so as to be rotatable about its central axis, while the entire core can rotate relative to last segment 14 to accommodate the required pivotal motion of last segment 14 relative to the head of the bolt. Thus, rotation of bolt 20 changes a degree of overlap between base 10 and bolt 20, thereby causing deflection of the sequence of segments.

This alternative mechanism may be used to implement each of the variant embodiments and features described above, whether for parallel motion or angular opening at either the distal or proximal end, and for all of the various applications described herein.

The use of the various implants of the present invention will now be self-evident to a person having ordinary skill in the art on the basis of the implant structure and various applications described herein above. In general terms, after preparation of the deployment volume, the implant is inserted into the body in its collapsed, closed state using a suitable implant holder tool (not shown) until correctly positioned within the target volume. An adjustment tool, for example with a hex-key tip or other screwdriver configuration designed to complement the form of head 24 of bolt 20 is engaged with the head and used to turn the bolt until a desired degree of expansion is achieved. The adjustment tool is typically removed, and where applicable, a quantity of biocompatible filler material is introduced into the implant. The holder is then released and withdrawn, and any required subsequent stages of the procedure are performed.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. An implant comprising:
 (a) a base;
 (b) a sequence of at least two segments including a first segment and a last segment, said first segment being pivotally linked to said base, adjacent segments of said sequence of segments being interconnected at pivotal connections; and
 (c) a bolt having a threaded shaft with a central axis and a head, said threaded shaft being engaged in a threaded channel of said base, wherein said last segment and said head define therebetween a spherical bearing such that rotation of said bolt about said central axis varies a degree of overlap between said base and said bolt, and causes deflection of said sequence of segments.

2. The implant of claim 1, wherein said sequence comprises only two segments.

3. The implant of claim 2, wherein a first of said two segments extends along a majority of a length of said sequence, and wherein a second of said two segments extends along less than half of the length of said sequence.

4. The implant of claim 3, wherein said first segment and said second segment are interconnected at a pivot axis, wherein said pivot axis is located within a medial 50% of a length of said first segment.

5. The implant of claim 1, wherein said sequence includes three segments.

6. The implant of claim 5, wherein said three segments comprise a major intermediate segment and first and last linking segments.

7. The implant of claim 6, further comprising a gear-tooth engagement to preserve parallel orientation of the intermediate segment to the base.

* * * * *